United States Patent [19]

Shin

[11] 4,401,814

[45] Aug. 30, 1983

[54] ADENINE PREPARATION

[75] Inventor: Kju H. Shin, Baton Rouge, La.

[73] Assignee: Ethyl Corporation, Richmond, Va.

[21] Appl. No.: 331,034

[22] Filed: Dec. 16, 1981

[51] Int. Cl.³ .......................................... C07D 437/74
[52] U.S. Cl. .................................................. 544/277
[58] Field of Search ........................ 544/277; 548/343

[56]  References Cited

U.S. PATENT DOCUMENTS

| | | | |
|---|---|---|---|
| 3,287,452 | 11/1966 | Wakamatsu et al. | 548/343 X |
| 3,398,149 | 8/1968 | Morita et al. | 544/277 |
| 3,671,649 | 6/1972 | Yamada et al. | 544/277 |
| 4,059,582 | 11/1977 | Yonemitsu et al. | 544/277 |
| 4,092,314 | 5/1978 | Zwan et al. | 544/277 |

FOREIGN PATENT DOCUMENTS 40-7915 7/1965 Japan.
50-135080 10/1975 Japan .................................. 544/277

OTHER PUBLICATIONS

Ochiai et al., Chemical Abstracts, vol. 72, 66987v, (1970).

*Primary Examiner*—Mark L. Berch
*Assistant Examiner*—Diana G. Rivers
*Attorney, Agent, or Firm*—Donald L. Johnson; John F. Sieberth; Willard G. Montgomery

[57]  ABSTRACT

Adenine is prepared by reacting a dinitrile of diaminomaleic acid with N-methyldichloroformidinium chloride and ammonia at elevated temperature in the presence of formamide and an ammonium salt of a lower alkanoic acid.

7 Claims, No Drawings

ADENINE PREPARATION

BACKGROUND

Adenine is widely present in the tissues of animals and plants as a main constituent of nucleic acids and coenzymes. Adenine and its derivatives also are known as having pharmacological effects and are very useful in the medical and biochemical fields.

There are serval known methods for producing adenine. For example, U.S. Pat. No. 3,287,452 discloses a method of producing adenine and 4,5-dicyanoimidazole which comprises reacting a source of hydrogen cyanide with ammonia in the liquid state in the absence of an amount of water greater than ten mole percent of the combined amounts of the hydrogen cyanide and the ammonia at a temperature of 60° C. to 150° C., wherein the mole ratio of ammonia to hydrogen cyanide is at least two to one.

U.S. Pat. No. 3,398,149 discloses a process for preparing adenine by heating formamide with a member selected from the group consisting of phosphorous trichloride, phosphorous oxychloride, phosphorous pentoxide, polyphosphoric acid, pyrophosphoric acid, tetrachloropyrophosphoric acid, thionyl chloride, sulfuryl chloride, chlorosulfonic acid and tosyl chloride within the range of from about at 70° C. to about 200° C. in a sealed vessel.

U.S. Pat. No. 3,427,315 discloses a process for preparing adenine or hypoxanthine wherein free formamidine is reacted in a non-aqueous solvent in the presence of ammonia with an α-amino-α-cyanoacetic acid derivative of the formula

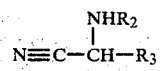

wherein $R_2$ is hydrogen, formyl, acetyl or propionyl, and $R_3$ is lower alkoxycarbonyl or carbamoyl.

U.S. Pat. No. 3,671,649 discloses a method of producing adenine and/or 4,5-dicyanoimidazole and derivatives thereof by reacting diaminomaleonitrile or diaminofumaronitrile with an amidine salt in an organic medium.

U.S. Pat. No. 4,059,582 discloses a process for preparing adenine by reacting at least one member selected from the class of diaminomaleonitrile and diaminofumaronitrile, a formic acid derivative and at least one member selected from the class of ammonia and ammonium salts in the presence or absence of a solvent.

U.S. Pat. No. 4,092,314 discloses a process for preparing 4,6-diamino-5-arylazopyromidine from an arylazomalonitrile in the presence of ammonium chloride and formamide. The 4,6-diamino-5-arylazopyrimidine may then be hydrogenated to form 4,5,6-triaminopyrimidine which, when the hydrogenation is carried out in the presence of formic acid or its derivative, gives adenine.

Japanese Patent Publication No. 42-7915 discloses a method of preparing adenine by reacting hydrogen cyanide with ammonia, or an alkali cyanide with ammonium salt and ammonia in the presence of formamide with heating.

Japanese Patent Publication No. 51-26897 discloses a method of preparing adenine by reacting diaminomaleonitrile or diaminofumaronitrile with formaldehyde in the presence of ammonia.

Of particular interest with respect to the present invention is aforementioned U.S. Pat. No. 3,671,649 which teaches a process for producing adenine (and 4,5-dicyanoimidazole) by reacting diaminomaleonitrile (DAMN) or diaminofumaronitrile (DAFN) with an amidine salt having the formula:

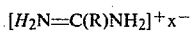

wherein R is hydrogen or a methyl group and X is an organic or inorganic acid with heating in an organic medium selected from the group consisting of an aliphatic lower alkyl alcohol having one to four carbon atoms, formamide, dimethylformamide, dimethylacetamide, dimethylaniline, anisole, dioxane and pyridine, and optionally in the presence of an ammonium salt of a lower alkanoic acid. The use of an amidine salt in this process is undesirable because of its relatively high cost. Thus, it would be highly desirable to employ a less expensive substitute for the amidine salt in the practice of the process and still obtain good yields of adenine. In accordance with the present invention, it has been found that N-dichloromethylformamidinium chloride and ammonia can be used in place of an amidine salt in the practice of the prior art process to give good yields of adenine while at the same time affording a cost savings over the use of an amidine salt.

SUMMARY

Thus, the present invention provides a process for the preparation of adenine by reacting a dinitrile of diaminomaleic acid with N-dichloromethylformamidinium chloride and ammonia at elevated temperature in the presence of formamide and an ammonium salt of a lower alkanoic acid.

The starting compound DAMN can be easily obtained in nearly quantitative yield by the polymerization of hydrogen cyanide in the presence of alumina (U.S. Pat. No. 2,499,441).

N-dichloromethylformamidinium chloride is a known compound and is easily synthesized in high yields by reacting 2 moles of liquid hydrogen cyanide with an excess of hydrogen chloride in ether at $-10°$ C. to $-15°$ C. It is expected that the salt gives 2 moles of formamidinium chloride when reacted with ammonia. N-dichloromethylformamidinium chloride is employed in an amount of from about 1 to 6 moles of N-dichloromethylformamidinium chloride per mole of DAMN.

The reaction proceeds when a mixture of DAMN, N-dichloromethylformamidinium chloride, ammonia and formamide is heated to 80° C. to 130° C., preferably about 100° C.

Formamide is employed in an amount of from about 30 ml to 200 ml, preferably 100 ml to 150 ml per mole of DAMN.

In general, from about 2 to 6 moles of ammonia per mole of DAMN are used in the practice of the present process. Conveniently, both the ammonia and the formamide can be added to the reaction mixture by forming an ammoniacal formamide solution containing the desired amounts of formamide and ammonia. Alternatively, liquid ammonia by itself can simply be added to the formamide-containing reaction mixture in the proper amounts.

As disclosed in U.S. Pat. No. 3,671,649, the yields of adenine are increased by the addition of an ammonium salt of a lower aliphatic carboxylic acid, such as ammonium formate, ammonium acetate and ammonium propionate. The usual addition amount of the ammonium salt is 0.5–20 (wt./vol.)% to the reaction mixture consisting of DAMN, N-dichloromethylformamidinium chloride, ammonia and formamide.

Adenine in the reaction mixture is quantitatively determined by HPLC with external standard. Qualitative analysis of the products is carried out with HPLC (Waters Associates, Inc., Model 244) using μ-Bondapak C18. The products are eluted with water/methanol (9/1) and detected by UV-detector. The work-up of the reaction mixture involves the following steps: centrifugation of the solids; evaporation of the volatiles and formamide solvent; solubilizing the residue with aqueous ammonium hydroxide; charcoal treatment; filtration; neutralization of the filtrate with hydrochloric acid; crystallization from the concentrated aqueous solution, and recrystallization from water.

The following examples are given solely for the purpose of illustration and are not to be construed as limitations of this invention.

EXAMPLE 1

DAMN (0.727 g; 0.1 mole), N-dichloromethylformamidinium chloride (0.12 g; 0.01 mole) and ammonium acetate (0.51 g; 0.01 mole) were charged to a 3 oz. Aerosol Compatibility Tube (Fischer and Porter Co.) at room temperature. An ammoniacal formamide solution consisting of 15 ml of formamide and 0.343 g ammonia was then added to the tube. The reaction was run for 2 hours at 100° C. with magnetic stirring. The mixture was cooled to 40° C. and a black solid by-product which formed during the reaction was filtered. HPLC indicated an adenine yield of 41.5%.

EXAMPLE 2

DAMN (0.86 g; 0.1 mole), N-methyldichloroformamidinium chloride (1.33 g; 0.1 mole), and ammonium acetate (0.61 g; 0.1 mole) were charged to a 3 oz. Aerosol Compatibility Tube (Fischer and Porter Co.) at room temperature. An ammoniacal formamide solution consisting of 17.8 ml formamide of 0.377 g of ammonia was then added to the tube. The reaction was run for 2 hours at 100° C. with magnetic stirring. The mixture was cooled to 40° C. and black solid by-product which formed during the reaction was filtered. HPLC indicated an adenine yield of 23.1%.

EXAMPLE 3

This example demonstrates that ammonia must be present in the process of the present invention in order to obtain adenine.

DAMN (0.23 g; 0.1 mole), N-methyldichloroformidinium chloride (0.8 g; 0.1 mole), ammonium acetate (0.37 g; 0.1 mole) and formamide (20 ml) were charged to a 3 oz. Aerosol Compatibility Tube (Fischer and Porter Co.) at room temperature. The reaction was run for 2 hours at 100° C. with magnetic stirring. The mixture was cooled to 40° C. HPLC indicated no adenine was formed by the reaction.

Having disclosed the process of the present invention, one skilled in the art can readily envision variations, modifications and changes within the scope and spirit of this invention. Therefore, it is desired that the present invention be limited only by the lawful scope of the following claims.

What is claimed is:

1. A process for the preparation of adenine which comprises reacting a dinitrile of diaminomaleic acid with N-dichloromethylformamidinium chloride and ammonia at elevated temperature in the presence of formamide and an ammonium salt of a lower alkanoic acid.

2. A process according to claim 1, wherein said N-dichloromethylformamidinium chloride is reacted with said dinitrile of diaminomaleic acid in an amount of from 1 to 6 moles of said N-dichloromethylformamidinium chloride per mole of said dinitrile of diaminomaleic acid.

3. A process according to claim 1, wherein said ammonium salt is present in the reaction mixture in an amount of about 0.5 to 20 grams per 100 ml.

4. A process according to claim 1, wherein said ammonium salt is ammonium acetate.

5. A process according to claim 1, wherein said formamide is present in the reaction mixture in an amount of from about 30 ml to 200 ml of formamide per mole of said dinitrile of diaminomaleic acid.

6. A process according to claim 1, wherein said ammonia is present in the reaction mixture in an amount of from about 2 to 6 moles of ammonia per mole of said dinitrile of diaminomaleic acid.

7. A process according to claim 1, wherein said elevated temperature is between about 80° C. and 200° C.

* * * * *

UNITED STATES PATENT AND TRADEMARK OFFICE
CERTIFICATE OF CORRECTION

PATENT NO. : 4,401,814
DATED : August 30, 1983
INVENTOR(S) : Kju Hi Shin

It is certified that error appears in the above—identified patent and that said Letters Patent is hereby corrected as shown below:

Abstract, line 2, "N-methyldichloroformidinium" should read -- N-dichloromethylformamidinium --.

Column 1, line 10, "serval" should read -- several --.

Column 3, line 47, "of 0.377g" should read -- and 0.377g --.

Column 4, lines 8 and 9, "N-methyldichloroformidinium" should read -- N-dichloromethylformamidinium --.

Signed and Sealed this

Twenty-seventh Day of December 1983

[SEAL]

Attest:

GERALD J. MOSSINGHOFF

*Attesting Officer*  *Commissioner of Patents and Trademarks*